(12) United States Patent
Underwood et al.

(10) Patent No.: US 6,766,202 B2
(45) Date of Patent: Jul. 20, 2004

(54) SYSTEMS AND METHODS FOR INTRADERMAL COLLAGEN STIMULATION

(75) Inventors: Ronald A. Underwood, Belmont, CA (US); Jean Woloszko, Mountain View, CA (US)

(73) Assignee: ArthroCare Corp., Sunnyvale, CA (US)

( * ) Notice: Subject to any disclaimer, the term of this patent is extended or adjusted under 35 U.S.C. 154(b) by 0 days.

(21) Appl. No.: 10/135,478

(22) Filed: Apr. 30, 2002

(65) Prior Publication Data

US 2002/0128641 A1 Sep. 12, 2002

Related U.S. Application Data

(60) Continuation of application No. 09/964,044, filed on Sep. 25, 2001, which is a division of application No. 09/464,884, filed on Dec. 16, 1999, now abandoned.
(60) Provisional application No. 60/151,484, filed on Aug. 30, 1999.

(51) Int. Cl.[7] .............................................. A61N 1/20
(52) U.S. Cl. ..................... 607/99; 607/113; 128/898; 606/32
(58) Field of Search .................. 606/32, 41; 607/99, 607/105, 113; 128/898

(56) References Cited

U.S. PATENT DOCUMENTS

| | | | |
|---|---|---|---|
| 2,050,904 A | 8/1936 | Trice | |
| 4,033,351 A | 7/1977 | Hetzel | 128/303 |
| 4,040,426 A | 8/1977 | Morrison, Jr. | 128/303 |
| 4,043,342 A | 8/1977 | Morrison, Jr. | 128/303 |
| 4,116,198 A | 9/1978 | Roos | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,248,231 A | 2/1981 | Herczog et al. | 128/303 |
| 4,326,529 A | 4/1982 | Doss et al. | 128/303.1 |
| 4,381,007 A | 4/1983 | Doss | 128/303.1 |

(List continued on next page.)

FOREIGN PATENT DOCUMENTS

| | | | |
|---|---|---|---|
| DE | 44 25 015 | 1/1998 | A61B/17/39 |
| EP | 515 867 | 12/1992 | A61B/17/36 |
| EP | 0 597 463 | 5/1994 | A61N/5/04 |

(List continued on next page.)

OTHER PUBLICATIONS

US 5,326,343, 7/1994, Rudie et al. (withdrawn)
Buchelt, M. et al. "Excimer Laser Ablation of Fibrocartilage: An In Vitro and In Vivo Study," (1991) Lasers in Surgery and Medicine 11:271–279.

(List continued on next page.)

*Primary Examiner*—Lee Cohen
(74) *Attorney, Agent, or Firm*—John T. Raffle; Richard R. Batt (57) ABSTRACT

The present invention provides systems, apparatus and methods for selective applying energy to a patient's dermis tissue to generate the growth of new collagen in this tissue, while minimizing the effect on the outer epidermis layer, thereby minimizing or suppressing the wound healing phase of the procedure. In one aspect of the invention, a method includes positioning a first electrode adjacent to, or in contact with, a region on or within a patient's skin, and applying a sufficient high frequency voltage between the first electrode and a second electrode to create a heat injury to a target tissue within the patient's dermis layer without ablating the epidermis layer overlying the target tissue. Typically, the voltage applied to the first and second electrodes is sufficient to induce heating of the dermis layer to about 60°–80° C., preferably about 65°–75° C. This induced heating causes the patient's body to undergo a wound healing response in the slightly inflamed tissue of the dermis. The wound healing process involves the generation of neo-collagen in the dermis layer, which fills in the wrinkle in the patient's skin.

15 Claims, 6 Drawing Sheets

U.S. PATENT DOCUMENTS

| | | |
|---|---|---|
| 4,476,862 A | 10/1984 | Pao .................. 128/303.17 |
| 4,532,924 A | 8/1985 | Auth et al. ............. 128/303 |
| 4,548,207 A | 10/1985 | Reimels ................ 128/303 |
| 4,567,890 A | 2/1986 | Ohta et al. .......... 128/303.13 |
| 4,593,691 A | 6/1986 | Lindstrom et al. .... 128/303.14 |
| 4,658,817 A | 4/1987 | Hardy ................. 128/303 |
| 4,674,499 A | 6/1987 | Pao .................... 128/303 |
| 4,682,596 A | 7/1987 | Bales et al. ............ 128/303 |
| 4,706,667 A | 11/1987 | Roos .................. 128/303 |
| 4,736,743 A | 4/1988 | Daikuzono ........... 128/303.1 |
| 4,737,678 A | 4/1988 | Hasegawa ............. 313/36 |
| 4,762,128 A | 8/1988 | Rosenbluth ........... 128/343 |
| 4,765,331 A | 8/1988 | Petruzzi et al. ........ 128/303 |
| 4,785,806 A | 11/1988 | Deckelbaum ......... 128/303.1 |
| 4,799,480 A | 1/1989 | Abraham et al. ....... 128/303 |
| 4,823,791 A | 4/1989 | D'amelio .............. 123/303 |
| 4,860,752 A | 8/1989 | Turner ................. 128/422 |
| 4,931,047 A | 6/1990 | Broadwin et al. ....... 604/22 |
| 4,936,301 A | 6/1990 | Rexroth et al. ......... 606/45 |
| 4,943,290 A | 7/1990 | Rexroth et al. ......... 606/45 |
| 4,955,377 A | 9/1990 | Lennox et al. ......... 128/401 |
| 4,967,765 A | 11/1990 | Turner et al. .......... 128/785 |
| 4,968,314 A | 11/1990 | Michaels ............... 606/7 |
| 4,976,711 A | 12/1990 | Parins et al. ........... 606/48 |
| 4,979,948 A | 12/1990 | Geddes et al. ......... 606/33 |
| 4,998,933 A | 3/1991 | Eggers et al. .......... 606/41 |
| 5,007,437 A | 4/1991 | Sterzer ................ 428/786 |
| 5,007,908 A | 4/1991 | Rydell ................. 606/47 |
| 5,009,656 A | 4/1991 | Reimels ................ 606/48 |
| 5,035,696 A | 7/1991 | Rydell ................. 606/47 |
| 5,037,421 A | 8/1991 | Boutacoff et al. ....... 606/15 |
| 5,057,105 A | 10/1991 | Malone et al. ......... 606/28 |
| 5,057,106 A | 10/1991 | Kasevich et al. ........ 606/33 |
| 5,059,192 A | 10/1991 | Zaias .................. 606/9 |
| 5,061,266 A | 10/1991 | Hakky ................. 606/15 |
| 5,065,515 A | 11/1991 | Iderosa ................. 30/140 |
| 5,078,717 A | 1/1992 | Parins et al. ........... 606/48 |
| 5,080,660 A | 1/1992 | Buelna ................. 606/48 |
| 5,083,565 A | 1/1992 | Parins ................. 128/642 |
| 5,098,431 A | 3/1992 | Rydell ................. 606/48 |
| 5,102,410 A | 4/1992 | Dressel ................ 606/15 |
| 5,108,391 A | 4/1992 | Flachenecker et al. .... 606/38 |
| 5,112,330 A | 5/1992 | Nishigaki et al. ........ 606/46 |
| 5,122,138 A | 6/1992 | Manwaring ............ 606/46 |
| 5,125,928 A | 6/1992 | Parins et al. ........... 606/48 |
| 5,143,063 A | 9/1992 | Fellner ................ 128/399 |
| 5,147,354 A | 9/1992 | Boutacoff et al. ....... 606/15 |
| 5,178,620 A | 1/1993 | Eggers et al. .......... 606/41 |
| 5,182,857 A | 2/1993 | Simon ................. 30/34 |
| 5,190,517 A | 3/1993 | Zieve et al. ............ 604/22 |
| 5,192,280 A | 3/1993 | Parins ................. 606/48 |
| 5,195,959 A | 3/1993 | Smith ................. 604/34 |
| 5,197,963 A | 3/1993 | Parins ................. 606/46 |
| 5,217,455 A | 6/1993 | Tan .................... 606/9 |
| 5,217,457 A | 6/1993 | Delahuerga et al. ...... 606/42 |
| 5,226,907 A | 7/1993 | Tankovich ............ 606/133 |
| 5,231,984 A | 8/1993 | Santana-Blank ........ 128/395 |
| 5,241,972 A | 9/1993 | Bonati ................ 128/898 |
| 5,249,585 A | 10/1993 | Turner et al. .......... 607/99 |
| 5,261,410 A | 11/1993 | Alfano et al. .......... 128/664 |
| 5,267,994 A | 12/1993 | Gentelia et al. ......... 606/15 |
| 5,267,997 A | 12/1993 | Farin et al. ............ 606/38 |
| 5,273,524 A | 12/1993 | Fox et al. ............. 604/21 |
| 5,277,201 A | 1/1994 | Stern .................. 607/98 |
| 5,281,216 A | 1/1994 | Klicek ................ 606/42 |
| 5,281,218 A | 1/1994 | Imran ................. 606/41 |
| 5,287,380 A | 2/1994 | Hsia ................... 372/69 |
| 5,290,273 A | 3/1994 | Tan .................... 606/9 |
| 5,290,282 A | 3/1994 | Casscells .............. 606/28 |
| 5,300,069 A | 4/1994 | Hunsberger et al. ...... 606/37 |
| 5,300,099 A | 4/1994 | Rudie ................. 607/101 |
| 5,301,687 A | 4/1994 | Wong et al. ........... 607/116 |
| 5,304,169 A | 4/1994 | Sand .................. 606/5 |
| 5,304,170 A | 4/1994 | Green ................. 606/9 |
| 5,312,395 A | 5/1994 | Tan et al. ............. 606/9 |
| 5,312,400 A | 5/1994 | Bales et al. ........... 606/41 |
| 5,314,406 A | 5/1994 | Arias et al. ........... 604/21 |
| 5,320,518 A | 6/1994 | Stilger et al. .......... 606/9 |
| 5,322,507 A | 6/1994 | Costello et al. ........ 128/4 |
| 5,324,254 A | 6/1994 | Phillips ............... 604/21 |
| 5,329,943 A | 7/1994 | Johnson .............. 128/898 |
| 5,330,470 A | 7/1994 | Hagen ................. 606/42 |
| 5,330,518 A | 7/1994 | Neilson et al. ......... 607/101 |
| 5,334,140 A | 8/1994 | Phillips ............... 604/35 |
| 5,334,183 A | 8/1994 | Wuchinich ............ 606/46 |
| 5,336,217 A | 8/1994 | Buys et al. ............ 606/9 |
| 5,336,220 A | 8/1994 | Ryan et al. ............ 604/22 |
| 5,342,357 A | 8/1994 | Nardella ............... 606/40 |
| 5,360,447 A | 11/1994 | Koop .................. 623/15 |
| 5,366,443 A | 11/1994 | Eggers et al. .......... 606/114 |
| 5,370,642 A | 12/1994 | Keller ................. 606/9 |
| 5,370,675 A | 12/1994 | Edwards et al. ........ 607/101 |
| 5,380,277 A | 1/1995 | Phillips ............... 604/33 |
| 5,380,316 A | 1/1995 | Aita et al. ............. 606/7 |
| 5,383,876 A | 1/1995 | Nardella ............... 606/49 |
| 5,383,917 A | 1/1995 | Desai et al. ........... 607/702 |
| 5,389,096 A | 2/1995 | Aita et al. ............. 606/15 |
| 5,395,312 A | 3/1995 | Desai ................. 604/22 |
| 5,417,687 A | 5/1995 | Nardella et al. ........ 606/32 |
| 5,419,767 A | 5/1995 | Eggers et al. .......... 604/114 |
| 5,423,803 A | 6/1995 | Tankovich et al. ...... 606/9 |
| 5,425,728 A | 6/1995 | Tankovich ............ 606/9 |
| 5,433,708 A | 7/1995 | Nichols et al. ......... 604/113 |
| 5,441,499 A | 8/1995 | Fritzsch ............... 606/45 |
| 5,445,634 A | 8/1995 | Keller ................. 606/9 |
| 5,454,809 A | 10/1995 | Janssen ................ 606/41 |
| 5,484,435 A | 1/1996 | Fleenor et al. ......... 606/46 |
| 5,490,850 A | 2/1996 | Ellman et al. ......... 606/45 |
| 5,507,790 A | 4/1996 | Weiss ................. 607/100 |
| 5,514,130 A | 5/1996 | Baker ................. 606/41 |
| 5,522,813 A | 6/1996 | Trelles ................ 606/3 |
| 5,556,397 A | 9/1996 | Long et al. ........... 606/48 |
| 5,569,242 A | 10/1996 | Lax et al. ............. 606/42 |
| 5,578,029 A | 11/1996 | Trelles et al. .......... 606/25 |
| 5,584,872 A | 12/1996 | LaFontaine et al. ..... 607/116 |
| 5,609,151 A | 3/1997 | Mulier et al. .......... 128/642 |
| 5,660,836 A | 8/1997 | Knowlton ............. 424/400 |
| 5,676,693 A | 10/1997 | LaFontaine ........... 607/116 |
| 5,681,282 A | 10/1997 | Eggers et al. .......... 604/114 |
| 5,683,366 A | 11/1997 | Eggers et al. .......... 604/114 |
| 5,683,386 A | 11/1997 | Ellman et al. ......... 606/41 |
| 5,683,387 A | 11/1997 | Garito et al. .......... 606/45 |
| 5,695,495 A | 12/1997 | Ellman et al. ......... 606/41 |
| 5,697,281 A | 12/1997 | Eggers et al. .......... 604/114 |
| 5,697,536 A | 12/1997 | Eggers et al. .......... 604/114 |
| 5,697,882 A | 12/1997 | Eggers et al. .......... 604/114 |
| 5,697,909 A | 12/1997 | Eggers et al. .......... 604/114 |
| 5,700,262 A | 12/1997 | Acosta et al. .......... 606/48 |
| 5,725,524 A | 3/1998 | Mulier et al. .......... 606/41 |
| 5,746,746 A | 5/1998 | Garito et al. .......... 606/41 |
| 5,749,869 A | 5/1998 | Lindenmeier et al. .... 606/34 |
| 5,755,753 A * | 5/1998 | Knowlton ............. 607/98 |
| 5,766,153 A | 6/1998 | Eggers et al. .......... 604/114 |
| 5,807,395 A | 9/1998 | Mulier et al. .......... 606/41 |
| 5,810,764 A | 9/1998 | Eggers et al. .......... 604/23 |
| 5,843,019 A | 12/1998 | Eggers et al. .......... 604/22 |
| 5,843,078 A | 12/1998 | Sharkey |
| 5,860,951 A | 1/1999 | Eggers et al. .......... 604/49 |
| 5,871,469 A | 2/1999 | Eggers et al. .......... 604/114 |
| 5,873,855 A | 2/1999 | Eggers et al. .......... 604/114 |
| 5,888,198 A | 3/1999 | Eggers et al. .......... 604/114 |

| | | | | |
|---|---|---|---|---|
| 5,891,095 A | 4/1999 | Eggers et al. | | 604/114 |
| 5,897,553 A | 4/1999 | Mulier et al. | | 606/41 |
| 5,902,272 A | 5/1999 | Eggers et al. | | 604/114 |
| 5,931,807 A | 8/1999 | McClure et al. | | 604/27 |
| 5,944,715 A | 8/1999 | Goble et al. | | 606/41 |
| 5,948,011 A | 9/1999 | Knowlton | | 607/101 |
| 6,004,319 A | 12/1999 | Goble et al. | | 606/48 |
| 6,013,076 A | 1/2000 | Goble et al. | | 606/41 |
| 6,015,406 A | 1/2000 | Goble et al. | | 606/41 |
| 6,024,733 A | 2/2000 | Eggers et al. | | 604/500 |
| 6,027,501 A | 2/2000 | Goble et al. | | 606/41 |
| 6,039,734 A | 3/2000 | Goble | | 606/41 |
| 6,047,215 A | 4/2000 | McClure et al. | | 607/101 |
| 6,056,746 A | 5/2000 | Goble et al. | | 606/48 |
| 6,066,134 A | 5/2000 | Eggers et al. | | 606/32 |
| 6,068,628 A | 5/2000 | Fanton et al. | | 606/41 |
| 6,074,386 A | 6/2000 | Goble et al. | | 606/34 |
| 6,090,106 A | 7/2000 | Goble et al. | | 606/41 |
| 6,093,186 A | 7/2000 | Goble | | 606/34 |
| 6,277,116 B1 * | 8/2001 | Utely et al. | | 606/42 |
| 6,283,987 B1 * | 9/2001 | Laird et al. | | 607/96 |

FOREIGN PATENT DOCUMENTS

| | | | | |
|---|---|---|---|---|
| EP | 0 703 461 A2 | 3/1996 | | G01R/27/02 |
| EP | 0 740 926 | 11/1996 | | A61B/17/39 |
| EP | 0 754 437 | 1/1997 | | A61B/17/39 |
| GB | 2308979 | 7/1997 | | A61B/17/39 |
| GB | 2308980 | 7/1997 | | A61B/17/36 |
| GB | 2308981 | 7/1997 | | A61B/17/39 |
| JP | 57-117843 | 7/1982 | | A61B/17/39 |
| WO | WO 90/07303 | 7/1990 | | A61B/17/39 |
| WO | WO 91/13650 | 9/1991 | | A61N/5/04 |
| WO | WO 92/21278 | 12/1992 | | A61B/5/04 |
| WO | WO 93/13816 | 7/1993 | | A61B/17/36 |
| WO | 93/20747 | 10/1993 | | A61B/5/00 |
| WO | WO 94/04220 | 3/1994 | | A61N/1/06 |
| WO | 94/08654 | 4/1994 | | A61M/37/00 |
| WO | 94/14383 | 7/1994 | | A61B/17/36 |
| WO | WO 94/26228 | 11/1994 | | A61G/17/36 |
| WO | 95/34259 | 12/1995 | | A61F/5/48 |
| WO | 96/00042 | 1/1996 | | A61B/17/39 |
| WO | 96/34568 | 11/1996 | | |
| WO | 97/00646 | 1/1997 | | A61B/17/39 |
| WO | 97/00647 | 1/1997 | | A61B/17/39 |
| WO | 97/15238 | 5/1997 | | A61B/17/39 |
| WO | 97/24073 | 7/1997 | | A61B/17/39 |
| WO | 97/24992 | 7/1997 | | A61B/17/38 |
| WO | 97/24993 | 7/1997 | | A61B/17/39 |
| WO | 97/24994 | 7/1997 | | A61B/17/39 |
| WO | 97/48346 | 12/1997 | | A61B/17/39 |
| WO | 98/07468 | 2/1998 | | |
| WO | 98/11944 | 3/1998 | | A61N/5/02 |
| WO | 98/27879 | 7/1998 | | A61B/17/36 |
| WO | 99/51155 | 10/1999 | | A61B/17/36 |
| WO | 99/51158 | 10/1999 | | A61B/17/39 |

OTHER PUBLICATIONS

Costello, A. J. et al. "Nd:YAG Laser Ablation of the Prostate as a Treatment of Benign Prostatic Hypertrophy," (1992) Lasers in Surger and Medicine 12:121–124.

P.C. Nardella (1989) *SPIE* 1068:42–49 Radio Frequency Energy and Impedance Feedback.

Rand et al. (1985) *J. Artho. Surg.* 1:242–246 Effect of Electrocautery on Fresh Human Articular Cartilage.

V.E. Elsasser et al. *Acta Medicotechnica* vol. 24, no. 4, pp. 129–134 (1976).

E.V. Kramolowsky et al. *J. of Urology* vol. 143, pp. 275–277 (1990).

J.W. Ramsey et al. *Urological Research* vol. 13, pp. 99–102 (1985).

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

E. Kramolowsky et al. (1991) *J. of Urology* 146:669–674.

J. Pearce *Electrosurgery*, (1986) John Wiley & Sons, New York, pp. 17, 69–75 and 87.

Slager et al. (1985) *JACC* 5(6): 1382–6.

Slager et al. (1987) *Z. Kardiol.* 76:Suppl. 6, 67–71.

* cited by examiner

SYSTEMS AND METHODS FOR INTRADERMAL COLLAGEN STIMULATION

RELATED APPLICATIONS

The present invention is a continuation of U.S. patent application Ser. No. 09/964,044, filed Sep. 25, 2001, which is a divisional of U.S. patent application Ser. No. 09/464, 884, filed Dec. 16, 199 now abandoned. U.S. patent application Ser. No. 09/464,884 derives priority from U.S. Provisional Patent Application No. 60/151,484 filed Aug. 30, 1999, the complete disclosures of which are incorporated herein by reference for all purposes.

The present invention is also related to commonly assigned U.S. patent application Ser. No. 08/990,374, filed Dec. 15, 1997, which is a continuation-in-part of U.S. patent application Ser. No. 08/485,219, filed on Jun. 7, 1995, now U.S. Pat. No. 5,697,281, U.S. patent application Ser. Nos. 09/109,219, 09/058,571, 09/248,763, 08/874,173 and 09/002,315, filed on Jun. 30, 1998, Apr. 10, 1998, Feb. 12, 1999, Jun. 13, 1997, and Jan. 2, 1998, respectively and U.S. patent application Ser. No. 09/054,323, filed on Apr. 2, 1998 , U.S. patent application Ser. No. 09/010,382, filed Jan. 21, 1998, and U.S. patent application Ser. No. 09/032,375, filed Feb. 27, 1998, U.S. application Ser. No. 08/942,580, filed on Oct. 2, 1997, U.S. application Ser. No. 08/753,227, filed on Nov. 22, 1996, U.S. application Ser. No. 08/687792, filed on Jul. 18, 1996, and PCT International Application, U.S. National Phase Serial No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992 which was a continuation-in-part of U.S. patent application Ser. No. 07/817,575, filed on Jan. 7, 1992, the complete disclosures of which are incorporated herein by reference for all purposes. The present invention is also related to commonly assigned U.S. Pat. No. 5,697,882, filed Nov. 22, 1995 the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat a patient's skin and subcutaneous tissue, particularly including skin resurfacing procedures.

In early dermatology procedures, cosmetic surgeons often employed chemical peels and/or dermabrasion techniques to remove outer layers of the patient's skin to rejuvenate wrinkled skin or to remove skins disorders, such as acne, lesions, early skin cancer, etc. These dermabrasion and chemical procedures, however, are difficult to control, requiring great surgical skill. In addition, these somewhat inelegant techniques often cause excessive bleeding, collateral tissue damage and patient discomfort.

In an effort to overcome some of the limitations of dermabrasion and chemical peels, lasers have been developed for use in cosmetic surgery. Lasers have improved the accuracy of skin resurfacing procedures, and they have reduced collateral damage to the tissue surrounding and underlying the treatment site. In laser dermatology applications, a handpiece is typically used to guide the output of a laser to the patient's skin, and to form a laser spot of a desired size on the region of the skin which is to be treated. The handpiece is typically attached to one end of an articulated arm which transmits the output of a medical laser (such as $CO_2$ or Er: YAG lasers) to the handpiece and allows the handpiece a wide range of motion.

Although initially encouraging, lasers suffer from a number of drawbacks in dermatology procedures. In the first place, laser equipment can be very expensive because of the costs associated with the laser light sources. Moreover, those lasers which permit acceptable depths of necrosis (such as excimer lasers, erbium: YAG lasers, and the like) provide a very low volumetric ablation rate, requiring numerous passes over the same treatment area which amounts to longer procedural times. In addition, erbium: YAG lasers generally do not provide effective hemostasis during the procedure, resulting in excessive bleeding which disrupts the surgeon's view of the treatment site. The $CO_2$ lasers provide a higher rate of ablation and an increased depth of tissue necrosis than their erbium: YAG counterparts. On the other hand, $CO_2$ lasers often create significant residual thermal injury to tissue at and surrounding the treatment site, which requires long healing periods for the patient. In addition, $CO_2$ lasers are associated with much pain and, therefore, require a lot of anesthesia, which increases the cost and length of the procedure.

Monopolar electrosurgical instruments have been used to effect electrodessication of abnormalities, such as lesions, skin tags, viral warts, pigment nevi, moles and skin cancer. For example, Conmed Corporation manufacturers a monopolar device, termed the Hyfrecator™ having a single active electrode at the tip of an electrosurgical probe. In these procedures, the skin abnormality is typically removed with a scalpel, and a low voltage is applied to the active electrode in contact with the target tissue to deliver electric current through the tissue and the patient to a dispersive pad or indifferent electrode. The voltage desiccates the remaining abnormal tissue, and coagulates severed blood vessels at the target site. The remaining tissue is then removed with a sponge or similar material. The voltage generally must be low enough to prevent charring and potential scarring of the underlying dermis.

These electrosurgical devices and procedures, however, suffer from a number of disadvantages. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. This cutting effect generally results in the production of smoke, or an electrosurgical plume, which can spread bacterial or viral particles from the tissue to the surgical team or to other portions of the patient's body. In addition, the tissue is parted along the pathway of evaporated cellular fluid, inducing undesirable collateral tissue damage in regions surrounding the target tissue site.

Another disadvantage with current techniques of skin resurfacing is that these techniques typically require the ablation or removal of all or at least a portion of the patient's epidermis layer. Removing the epidermis provides some beneficial effects, such as allowing for the creation of a neo-epidermis, removing or reducing sun discolorations and improving the superficial skin texture. However, this removal of the epidermis layer necessitates the use of wound dressing until a new epidermis is created, which greatly increases the pain and lengthens the healing time of the procedure.

SUMMARY OF THE INVENTION

The present invention provides systems, apparatus and methods for selectively applying electrical energy to structures on the external surface of a patient's body. The systems and methods of the present invention are particularly useful in skin resurfacing, i.e., removing or reducing wrinkles in the patient's dermis tissue. The techniques of the present invention generally involve the selected application of energy to the patient's dermis tissue to generate the growth of new collagen in this tissue, while minimizing the energy applied to the outer epidermis layer, thereby minimizing or suppressing the wound healing phase of the procedure.

In one aspect of the invention, a method includes positioning a first electrode adjacent to, or in contact with, a region on or within a patient's skin, and applying a sufficient high frequency voltage between the first electrode and a second electrode to create a heat injury to a target tissue within the patient's dermis layer without ablating the epidermis layer overlying the target tissue. Typically, the voltage applied to the first and second electrodes is sufficient to induce heating of the dermis layer to about 60°–80° C., preferably about 65°–75° C. This induced heating causes the patient's body to undergo a wound healing response in the slightly inflamed tissue of the dermis. The wound healing process involves the generation of neo-collagen in the dermis layer, which fills in the wrinkle in the patient's skin. In the present invention, this stimulation of collagen growth within the dermis is accomplished while minimizing or suppressing the damage caused to the outer epidermis layer, which reduces the overall pain and wound healing time for the patient.

In one embodiment, the first and second electrodes are positioned on the outer surface of the patient's skin, and high frequency voltage is applied therebetween. The electrodes are spaced, sized and otherwise configured such that an electric current passes from the first electrode, through the epidermis layer to the target tissue in the dermis layer, and to the second electrode. Specifically, electrodes are selected with large surface areas that present a substantially uniform current density to minimize high current densities at the electrode surfaces, thereby generating a maximum current density within the dermis. The electrodes are spaced a sufficient distance to allow the electric current to penetrate the epidermis and pass through the dermis. In a preferred embodiment, the electrodes are positioned on either side of a wrinkle in the patient's skin, and translated along the length of the wrinkle as high frequency voltage is applied therebetween.

In the representative embodiment, the first and second electrodes comprise spherical or hemispherical electrodes coupled to electrode support members that separate the electrodes from each other by a selected distance, typically about 5 to 20 cm. The spherical electrodes have a smooth outer surface to minimize current densities on this surface and to provide a homogenous current distribution around the electrodes. The electrode support members typically comprise a conductive shaft surrounded by an insulating jacket, or an insulating shaft that houses the electrical connections. The electrode support members service to electrically and mechanically couple the electrodes to a probe or handpiece for manipulation by the physician. The handpiece or probe is, in turn, coupled to a high frequency power supply for applying high frequency voltage through the handpiece to the electrodes. In one embodiment, the distance between the electrodes may be varied by the physician through an input control on the handpiece.

In a specific configuration, electrically conductive fluid is provided between each of the first and second electrodes and the patient's skin to improve the contract between the electrodes and the skin. In one embodiment, an electrically conductive gel is applied to the skin surface to create a low impedance current path through the gel. In another embodiment, a conductive hydrogel is coated on the electrode surfaces. The hydrogel may also be soaked within a conductive fluid, such as isotonic saline, to create a slippery conductive interface with the patient's skin, while minimizing skin surface conduction. The hydrogel does not retain as much heat as a conventional gel on the skin, which reduces the thermal injury to the patient's skin.

In another embodiment, the first electrode is advanced through the patient's epidermis layer to the underlying dermis layer, and high frequency voltage is applied between the first and second electrodes to effect heating of the dermis layer. In this embodiment, the first electrode functions as an active electrode and the second electrode functions as the return electrode. The first electrode comprises a sharp tapered distal end for mechanically advancing a portion of the electrode through the skin to the dermis layer. The second or return electrode may be a dispersive return pad positioned on the surface of the patient's skin. In another embodiment, the second electrode is also advanced through the patient's epidermis layer to the underlying dermis such that the electric current is confined to the dermis layer. In these embodiments, both electrodes may have similar shapes, and thus, both function as active or bi-active electrodes. In some embodiments, additional active and/or return electrodes may be advanced into the patient's skin to more precisely control the heat injury within the dermis.

In a specific configuration, an electrode array of needle-shaped electrodes are advanced through the epidermis into the underlying dermis. The outer periphery of needle electrodes have a separate polarity from one or more of the inner electrodes to cause current flow therebetween. This configuration confines the current flow to an area within the electrode array.

In the representative embodiment, an electrosurgical probe or handpiece comprises a shaft or handle coupled to an electrode support at the distal end of the shaft or handle. The electrode support mechanically and electrically couples an electrode assembly to the probe or handpiece. The electrode assembly comprises an array of needle shaped electrodes designed for advancing through the patient's skin. In this embodiment, the needle shaped electrodes include a proximal insulated portion for minimizing electric contact with the epidermis, and a distal exposed portion for applying electric current to the underlying dermis. In some embodiments, the probe will include a stop or other mechanism for controlling the depth of penetration of the electrodes in the patient's skin.

A further understanding of the nature and advantages of the invention will become apparent by reference to the remaining portions of the specification and drawings.

DESCRIPTION OF SPECIFIC EMBODIMENTS

The present invention provides systems and methods for selectively applying electrical energy to a target location within or on a patient's body, particularly including procedures on an external body surface, such as collagenous tissue within the eye and epidermal and dermal tissues in the skin. For convenience, the remaining disclosure will be directed specifically to the stimulation of collagen growth in the epidermis or dermis. However, it will be appreciated that the system and method can be applied equally well to procedures involving other tissues of the body, as well as to other procedures including open procedures, intravascular procedures, interventional cardiology procedures, urology, laparascopy, arthroscopy, thoracoscopy or other cardiac procedures, cosmetic surgery, orthopedics, gynecology, otorhinolaryngology, spinal and neurologic procedures, oncology and the like.

The present invention applies high frequency (RF) electrical energy to one or more active electrodes adjacent an external body surface, such as the outer surface of the skin, to modify the structure of tissue structures within the skin. The techniques of the present invention generally involve the selected application of energy to the patient's dermis tissue to generate the growth of new collagen in this tissue, while minimizing the effect on the outer epidermis layer, thereby minimizing or suppressing the wound healing phase of the procedure.

In one aspect of the invention, a method includes positioning a first electrode adjacent to, or in contact with, a region on or within a patient's skin, and applying a sufficient high frequency voltage between the first electrode and a second electrode to create a heat injury to a target tissue within the patient's dermis layer without ablating the epidermis layer overlying the target tissue. In these procedures, it is desirable to stimulate the growth of neo-collagen in the tissue layers underlying the epidermal tissue. Thus, the temperature of the electrode terminal(s) are carefully controlled such that sufficient thermal energy is transferred to these underlying layers to contract, damage or otherwise injure these layers such that the body regrows collagen in this region. The thermal energy may be transferred directly through RF current that passes through and resistively heats the underlying tissue layers, or it may be transferred indirectly by heating electrically conducting fluid within the dermis. Collagen growth within the skin typically occurs after the area has been heated to temperatures in the range of about 40° C. to about 65° C.

The electrosurgical instrument of the present invention comprises a shaft or a handpiece having a proximal end and a distal end which supports one or more electrode(s). The shaft or handpiece may assume a wide variety of configurations, with the primary purpose being to mechanically support the electrode(s) and permit the treating physician to manipulate the electrode(s) from a proximal end of the shaft. For cosmetic surgery or dermatology procedures, the shaft will have any suitable length and diameter that would facilitate handling by the surgeon.

The active electrode(s) are preferably supported by, or within, an insulating support positioned near the distal end of the instrument shaft. The device may include two or more active electrode(s) that function as the active and the return portion of the electrical circuit (similar to the bi-active electrodes on conventional bipolar forceps). Alternatively, one or more of the electrode(s) may be sized and shaped to function more as a return electrode, with little or no current densities on the surface of the return electrode. In these embodiments, the return electrode may be located on the instrument shaft, on another instrument, or on the external surface of the patient (i.e., a dispersive pad). In most applications, applicant has found that it is preferably to have the return electrode on or near the shaft of the instrument to confine the electric currents to the target site. In some applications and under certain conditions, however, the invention may be practiced in a monopolar mode, with the return electrode attached to the external surface of the patient. The proximal end of the instrument will include the appropriate electrical connections for coupling the return electrode(s) and the active electrode(s) to a high frequency power supply, such as an electrosurgical generator.

The voltage applied between the return electrode and the electrode array will be at high or radio frequency, typically between about 5 kHz and 20 MHz, usually being between about 30 kHz and 2.5 MHz, preferably being between about 50 kHz and 600 kHz, in some embodiments less than 350 kHz, and, in exemplary embodiments between about 100 kHz and 200 kHz. The RMS (root mean square) voltage applied will usually be in the range from about 5 volts to 1000 volts, preferably being in the range from about 10 volts to 500 volts depending on the electrode sizes, the operating frequency and the operation mode of the particular procedure or desired effect on the tissue (i.e., contraction). Typically, the peak-to-peak voltage will be in the range of 10 to 2000 volts and preferably in the range of 20 to 800 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, the total number of electrode(s) and/or the maximum allowed temperature selected for the probe tip. The power source allows the user to select the voltage level according to the specific requirements of a particular procedure. A description of a suitable power source can be found in U.S. patent application Ser. No. 09/058,571, filed on Apr. 10, 1998 (Attorney Docket No. CB-2), the complete disclosure of which has been previously incorporated herein by reference.

Figure 1:
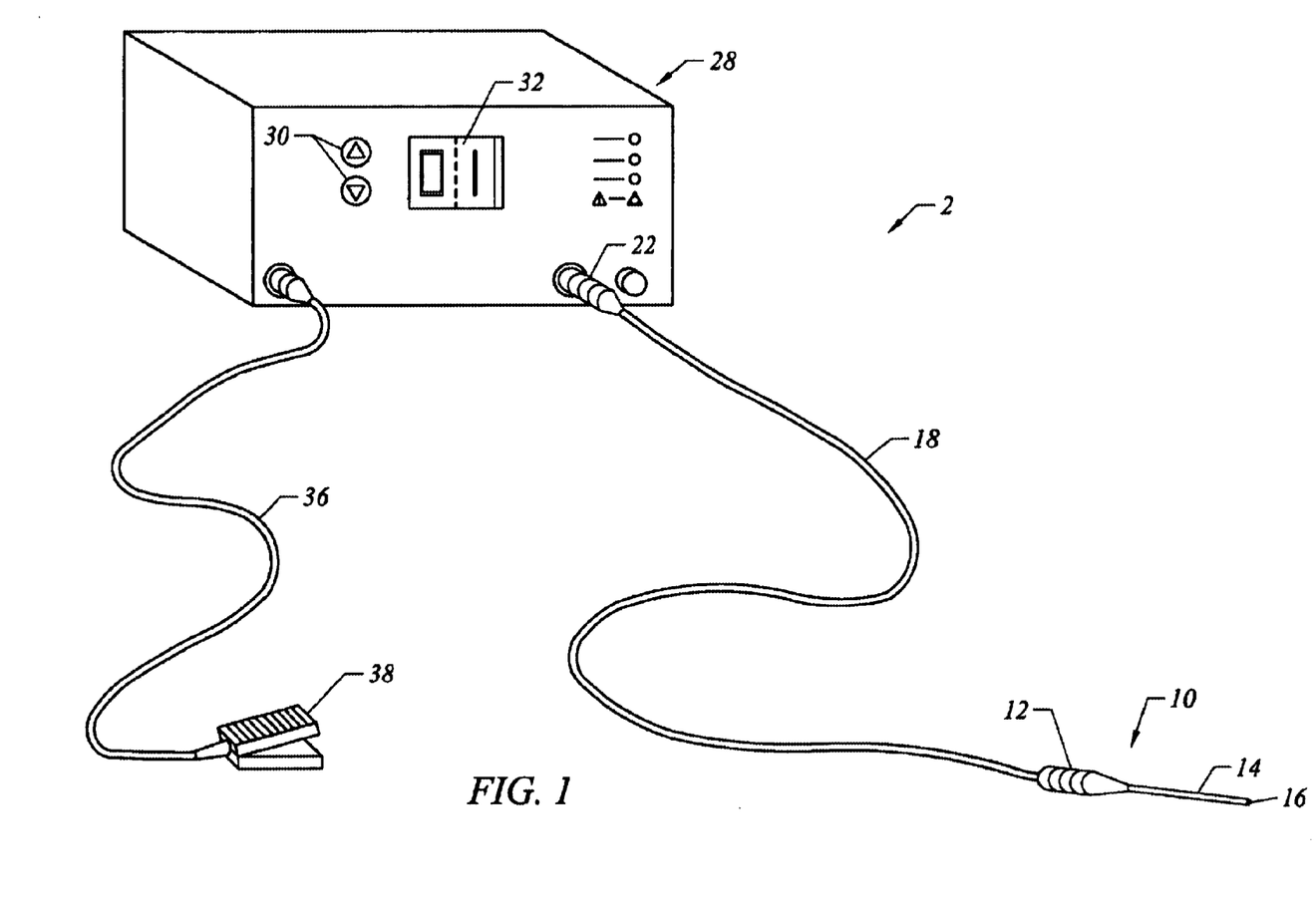
FIG. 1 is a perspective view of an electrosurgical system according to the present invention incorporating a high frequency power supply and an electrosurgical invention for treating the patient.

Referring to FIG. 1, an electrosurgical system 2 generally comprises an electrosurgical handpiece or probe 10 connected to a power supply 28 for providing high frequency voltage to a target site. Probe 10 generally includes a proximal handle 12 and an elongate shaft 14 for supporting an electrode assembly 16 at the distal end of shaft 14. A connecting cable 18 has a connector 22 for electrically coupling the electrodes in electrode assembly 16 to power supply 28. Power supply 28 has an operator controllable voltage level adjustment 30 to change the applied voltage level, which is observable at a voltage level display 32. Power supply 28 also includes an operator input, preferably a foot pedal 38, and a cable 36 which removably couples foot pedal 38 to power supply 28. The foot pedal 38 allows the surgeon to remotely adjust the energy level applied to electrode assembly 16. Of course, it will be recognized that the voltage and modality of the power supply may be controlled by other input devices. However, applicant has found that foot pedals are convenient methods of controlling the power supply while manipulating the probe during a surgical procedure.

The power supply generally comprises a radio frequency (RF) power oscillator (not shown) having output connections for coupling via a power output signal to the load impedance, which is represented by the electrode assembly when the electrosurgical probe is in use. In the representative embodiment, the RF oscillator operates at about 100 kHz. The RF oscillator is not limited to this frequency and may also operate at frequencies of about 300 kHz to 600 kHz. The RF oscillator will generally supply a square wave signal with a crest factor of about 1 to 2. Of course, this signal may be a sine wave signal or other suitable wave signal depending on the application and other factors, such as the voltage applied, the number and geometry of the electrodes, etc. The power output signal is designed to incur minimal voltage decrease (i.e., sag) under load. This improves the applied voltage to the electrode terminals and the return electrode, which improves the rate of volumetric removal (ablation) of tissue.

Power is supplied to the oscillator by a switching power supply (not shown) coupled between the power line and the RF oscillator rather than a conventional transformer. The switching power supply allows the generator to achieve high peak power output without the large size and weight of a bulky transformer. The architecture of the switching power supply also has been designed to reduce electromagnetic noise such that U.S. and foreign EMI requirements are met. This architecture comprises a zero voltage switching or crossing, which causes the transistors to turn ON and OFF when the voltage is zero. Therefore, the electromagnetic noise produced by the transistors switching is vastly reduced. In an exemplary embodiment, the switching power supply operates at about 100 kHz.

A controller (not shown) coupled to the operator controls (i.e., foot pedals and voltage selector) and display, is connected to a control input of the switching power supply for adjusting the generator output power by supply voltage variation. The controller may be a microprocessor or an integrated circuit. The power supply may also include one or more sensors for detecting the output current or voltage. The power supply is preferably housed within a metal casing which provides a durable enclosure for the electrical components therein. In addition, the metal casing reduces the electromagnetic noise generated within the power supply because the grounded metal casing functions as a "Faraday shield", thereby shielding the environment from internal sources of electromagnetic noise.

The power supply generally comprises a main or mother board containing generic electrical components required for many different surgical procedures (e.g., arthroscopy, urology, general surgery, dermatology, neurosurgery, etc.), and a daughter board containing application specific current-limiting circuitry (e.g., inductors, resistors, capacitors and the like). The daughter board is coupled to the mother board by a detachable multi-pin connector to allow convenient conversion of the power supply to, e.g., applications requiring a different current limiting circuit design.

In some embodiments, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

The power output signal may also be coupled to a plurality of current limiting elements, which are preferably located on the daughter board since the current limiting elements may vary depending on the application. In the representative embodiment, the current limiting elements are inductors having an inductance in the range of about 100 to 5000 microhenries, with the particular value depending on the electrode terminal dimensions, the desired ablation rates, and the like. Capacitors having capacitance values in the range of about 200 to 10,000 picofarads may also be used as the current limiting elements. It would also be possible to use resistors as current limiting elements. The current limiting elements any also be part of a resonant circuit structure, as described in detail in the '909 patent.

Figure 2:
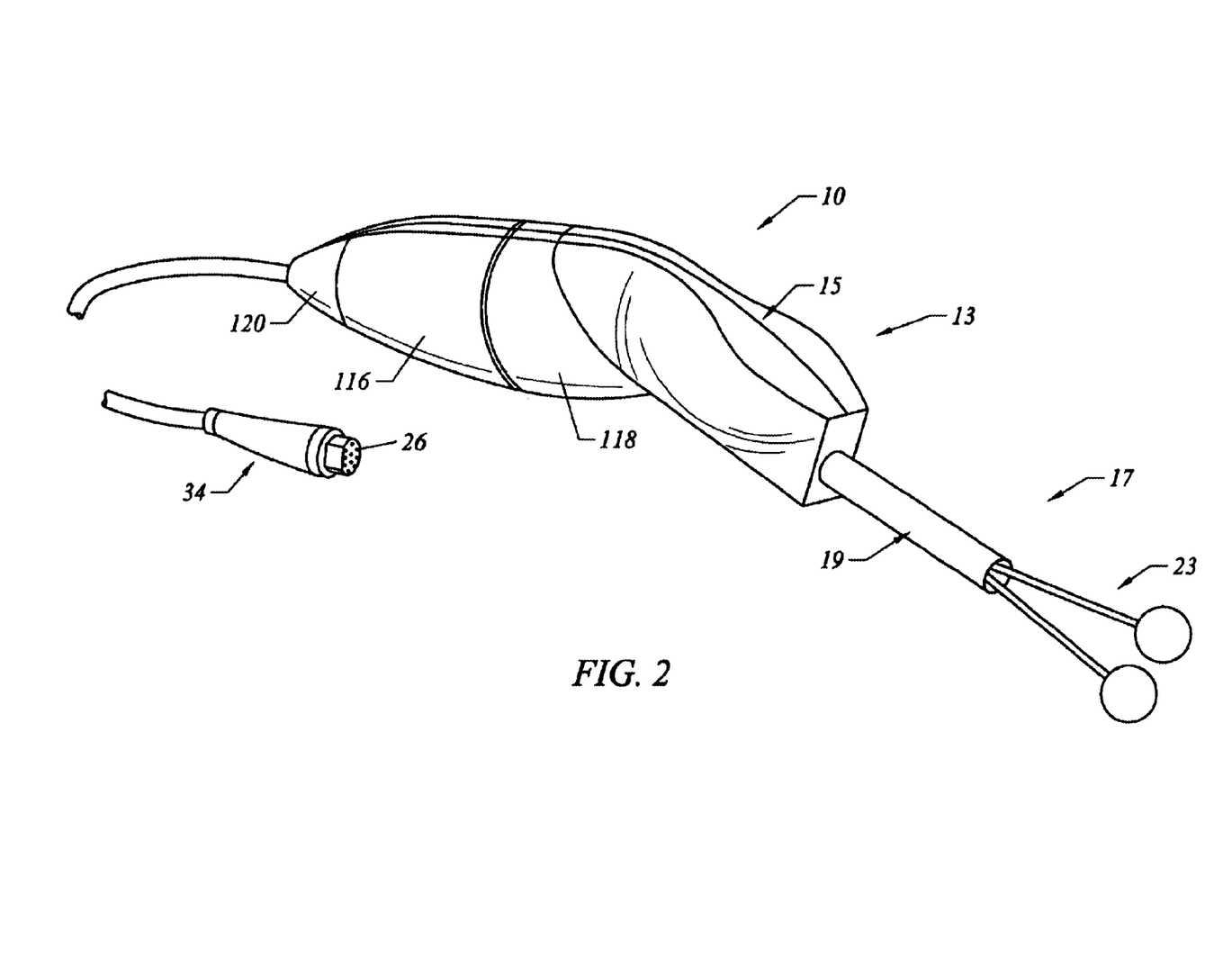
FIG. 2 is a perspective view of one electrosurgical probe or handpiece according to the present invention.

Referring now to FIG. 2, an exemplary electrosurgical probe 10 comprises a shaft or disposable tip 13 removably coupled to a proximal handle 12.). Probe 10 will typically include a coding resistor (not shown) having a value selected to program different output ranges and modes of operation for the power supply 28. This allows a single power supply to be used with a variety of different probes in different applications (e.g., skin resurfacing, tissue incision, tissue ablation, tissue heating, etc). Disposable tip 13 includes a proximal housing 15 designed for coupling with handle 12, and a distal working portion 17 for treating the patient. In this embodiment, the distal working portion 17 includes a shaft 19 extending from proximal housing 15 and an electrode assembly 23 extending from the distal end of shaft 19. Tip 13 and handle 12 typically comprise a plastic material that is easily molded into a suitable shape for handling by the surgeon. Handle 12 defines an inner cavity (not shown) that houses the electrical connections (not shown), and provides a suitable interface for connection to electrical connecting cable 18 (see FIG. 1). In the exemplary embodiment, handle 12 is constructed of a steam autoclavable plastic or metal (e.g., polyethylether keytone, or a stable metal alloy containing aluminum and/or zinc) so that it can be re-used by sterilizing handle 12 between surgical procedures. High service temperature materials are preferred, such as a silicone cable jacket and a poly-ether-imide handpiece or ULTEM® that can withstand a repeated exposure to high temperatures. A more complete description of a suitable handle can be found in commonly-assigned copending application Ser. No. 08/977,845 (D-2), previously incorporated herein by reference.

Figure 3:
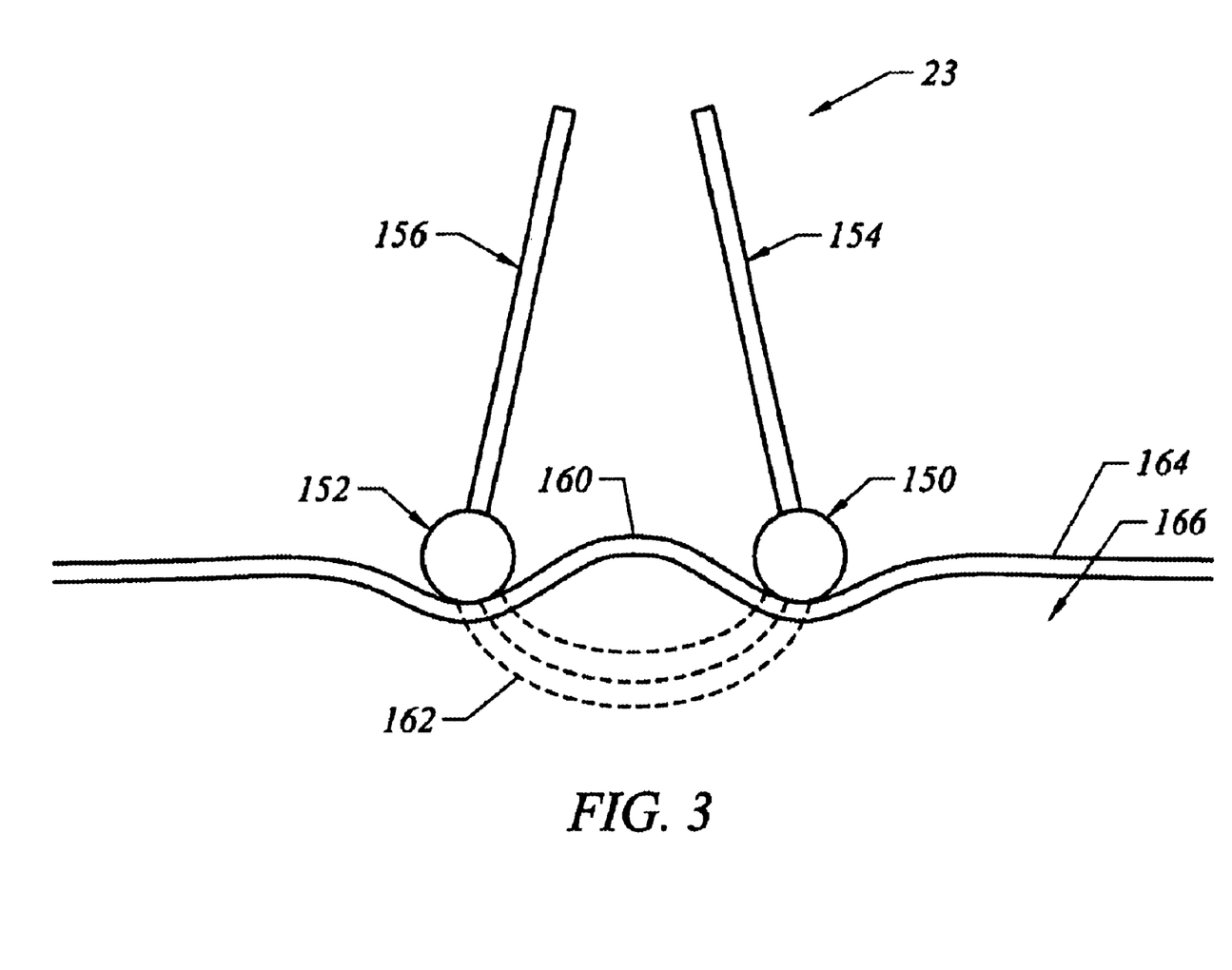
FIG. 3 is an enlarged view of an electrode assembly of the probe of FIG. 2, illustrating a method of treating wrinkles according to the present invention.

Referring now to FIG. 3, electrode assembly 23 preferably comprises first and second electrodes 150, 152 each coupled to an electrically insulating support member 154, 156, respectively, that extends from the distal end of shaft 19 (FIG. 2). Support members 154, 156 are preferably configured to extend at an angle to the shaft axis such that electrodes 150, 152 are spaced from each other. Electrodes 150, 152 are preferably spaced a sufficient distance to allow current flow 162 from one of the electrodes, through the patient's dermis layer, to the other of the electrodes (discussed in more detail below). In the representative embodiment, electrodes 150, 152 are spaced a distance of about 5 to 30 mm. In alternative embodiments, the spacing of the electrodes 150, 152 may be varied by the physician. This can be accomplished in a variety of manners, e.g., allowing axial movement of the electrode assembly 23 relative to shaft 19 to change the angle of support members 154, 156.

Electrodes 150, 152 have a relatively large surface area and shape that will present a uniform current density and minimize or eliminate any sharp edges or irregular surfaces that would generate high current densities at the electrode surfaces. As shown in the representative embodiment, electrodes 150, 152 are spherical, and have a diameter in the range of about 1 to 20 mm. Of course, the size and shape of the electrodes will, at least in part, depend on the application (i.e., the location of the skin to be treated) and the voltage applied. For example, electrodes may have a variety of shapes, such as hemispherical, concave, convex, planar and the like. Alternatively, the electrodes may be substantially flush with the electrode support to minimize current densities at the electrode surfaces. In this embodiment, both electrodes 150, 152 almost function as return electrodes in the sense that they do not ablate or otherwise treat the skin immediately adjacent to, or in contract with, the electrodes 150, 152.

In use, electrodes 150, 152 are positioned adjacent to, or in contact with, a target area on the patient's skin. In some embodiments, electrodes 150, 152 will be positioned so as to straddle a wrinkle 160 in the patient's skin. High frequency voltage is then applied from the power supply 28 to the electrodes 150, 152 such that an electric current passes from one of the electrodes, through the epidermis 164 and the dermis 166, to the other electrode. With the electrode assembly described in FIG. 3, the voltage level is about 10 to 2000 volts peak to peak, typically about 20 to 800 volts peak to peak. In some embodiments, the voltage difference will be sufficient to elevate the tissue temperature from normal body temperatures (e.g., 37° C.) to temperatures in the range of 45° C. to 90° C., preferably in the range from 55° C. to 70° C. and, for the case of skin, preferably in the range of about 60° C. to 80° C. This temperature elevation causes sufficient damage to the collagen connective fibers to enhance or stimulate regrowth of new collagen fibers in the underlying tissue.

Electric current generally flows through low impedance paths, and will concentrate in highly hydrated tissue or organs (e.g., vessels, muscles, etc). The dermis layer is substantially more conductive than the epidermis. Therefore, most of the electric current 164 between electrodes 150, 152 will rapidly pass through the epidermis 164 and flow through the lower impedance dermis 166, as shown in FIG. 3. The large, uniform surface area of the electrodes 150, 152 allows current to be injected through the epidermis layer to the dermis with minimal heat generation at the high impedance epidermis. Thus, the maximum current density will be observed in the dermis. This allows the physician to create a controlled dermis heat injury, while minimizing the damage to the epidermis.

During the procedure, the physician preferably translates the electrodes 150, 152 in a direction parallel to the wrinkle 160 to cause a heat injury in the dermis along the entire length of the wrinkle. The rate of movement of the electrodes will have an effect on the amount of energy delivered to the dermis as temperature or heating is a function of the time in which heat is applied. Of course, this effect will also depend on the voltage level, the distance between the electrodes and the size and shape of the electrodes. In the configuration described above, the electrodes 150, 152 are preferably translated at a rate of about 0.5 to 5.0 m/s.

In some embodiments, an electrically conductive fluid will be applied at, or delivered to, the interface between the electrodes 150, 152 and the skin surface to improve the electrical contact therebetween and thus further reduce the heat generated at the epidermis. In one embodiment, an electrically conductive gel is applied to the skin surface to create a low impedance current path through the gel. In another embodiment, the electrode surfaces are coated with a highly conductive hydrogel. In one embodiment, the hydrogel is soaked with saline either using a very slow drip or by soaking the electrodes in a small saline bath prior to use. The hydrogel creates a slippery, conductive interface with the skin, while minimizing skin surface conduction. In addition, the saline (which can be cooled) will help to prevent heating of the hydrogel, reducing thermal injury to the skin surface from heated gel.

Figure 4:
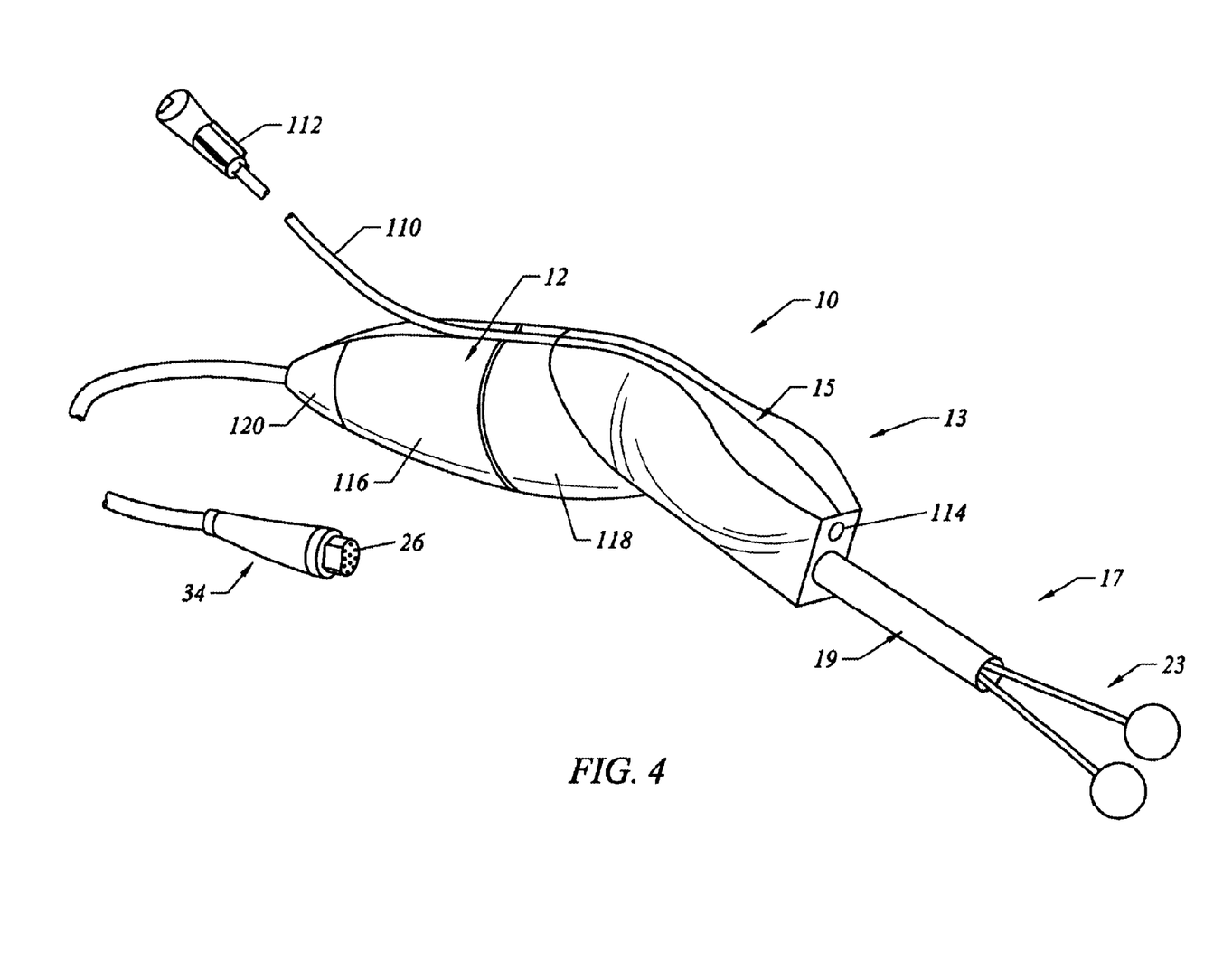
FIG. 4 is an alternative embodiment of the probe of FIG. 2, incorporating a fluid delivery tube.

In an alternative embodiment, electrically conductive fluid is delivered to the target site to increase the conductivity between electrodes 150, 152 and the epidermis. As shown in FIG. 4, probe 10 includes a fluid tube 110 for delivering electrically conductive fluid to the target site. Fluid tube 110 is sized to extend through a groove 114 in handle 13 and through the inner cavity of tip 13 to a distal opening 114 located adjacent shaft 19. Tube 110 extends all the way through the inner cavity to opening 114 to eliminate any possible fluid ingress into the cavity. Fluid control may be provided by a variety of input and valve devices, such as switches, buttons, etc. The probe may further include a suction lumen (not shown) for aspirating excess fluid, bubbles or blood from the target site during the procedure.

In another embodiment, the electrodes 150, 152 are rotatably coupled to support members 154, 156 to allow for rotation. In a preferred embodiment, electrodes 150, 152 rotate freely in a socket (not shown), and saline or conductive gel is injected through the socket to improve the conductivity at the electrode/skin interface.

Figure 5:
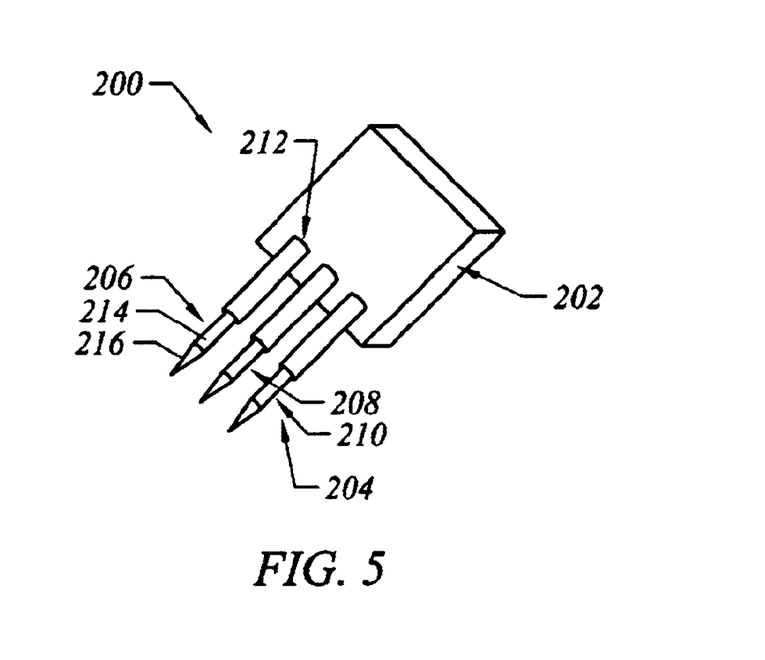
FIG. 5 is a perspective view of a second electrode assembly according to the present invention.

Referring now to FIGS. 5–8, another embodiment of the present invention is illustrated. As shown in FIG. 5, a disposable tip 200 comprises an electrode support 202 coupled to an electrode assembly 204. The electrode support 202 includes a mechanical connection (not shown) for attaching disposable tip to an instrument (not shown), such as the instruments described above or other suitable handpieces or probes designed for handling by the physician. Electrode support 202 further includes the necessary electrical connections (not shown) for coupling electrode assembly 204 to a power supply through a handpiece or probe. As shown, electrode assembly 204 comprises three needle shaped electrodes 206, 208, 210 extending from three guards 212 that are attached to electrode support 202. As discussed in detail below, guards 212 function as stops to prevent the physician from advancing electrodes 206, 208, 210 beyond a selected depth in the patient's skin. Electrodes 206, 208, 210 will each include a proximal insulated portion 214 and a distal exposed portion 216 for applying electric current to the patient.

In use, electrode assembly 204 is positioned adjacent to the target area of the patient's tissue. Electrodes 206, 208, 210 are then advanced through the epidermis 164 such that the exposed portion 216 of each electrode is positioned in the dermis 166 at a selected depth. In the representative embodiment, electrodes 206, 208, 210 are advanced manually by the physician by advancing the entire disposable tip. Guards 212 have larger diameters than electrodes 206, 208, 210 such that physician will feel the additional resistance when guards 212 are in contact with the outer skin surface and the electrodes are in the selection position in the dermis. In alternative embodiments, the electrodes may be axially movable relative to the guards or the electrode support 202. In these embodiments, the guards or electrode support are placed against the patient's skin, and the electrodes are then advanced axially from the guards or electrode support a selected distance into the patient's skin.

The insulated portions 214 of each electrode help prevent current from being applied to non-target areas in the skin, such as the epidermis 164. The dimensions of the electrodes and guards will, of course, depend on the application, the voltage level and other factors. In the representative embodiment, electrodes 206, 208, 210 will have an exposed length in the range of about 0.5 to 10, and the insulated portion will have a length in the range of about 0.5 to 10. Electrodes 206, 208, 210 will taper down to a point to facilitate the penetration into the tissue. The insulating portion will typically comprise a conductive shaft surrounded by an insulating member, which is typically formed as one or more electrically insulating sheaths or coatings, such as polytetrafluoroethylene, polyimide, and the like. The provision of the electrically insulating jacket over the conductive shaft prevents direct electrical contact between these metal elements and any adjacent body structure, such as the epidermis. Such direct electrical contact between a body structure and an exposed electrode could result in unwanted heating and necrosis of the structure at the point of contact causing necrosis.

Figure 6:
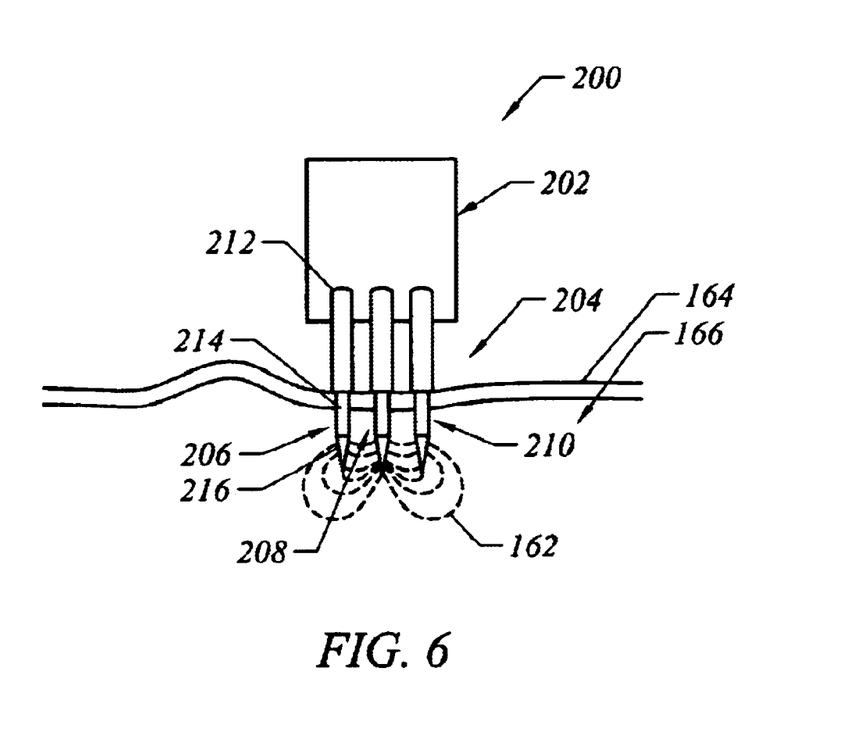
FIG. 6 is an enlarged view of the electrode assembly of FIG. 5, illustrating another method of treating wrinkles according to the present invention.

As shown in FIG. 6, the central electrode 208 has an opposite polarity from the outer electrodes 206, 210 such that electric current 162 flows between central electrode 208 and outer electrodes 206, 210 when a voltage is applied therebetween. In this manner, the current is generally confined to the immediate region around the electrodes which is the target area of the dermis 166. The voltage level will be selected to induce heating of the dermis 166 to a temperature in the range of about 60° to 80° C., typically about 65° to 75° C., without causing necrosis, ablation or vaporization of the tissue. As in previous embodiments, electrically conductive fluid (e.g., saline) may be delivered to the target site to modify the impedance of the tissue, if desired.

Figure 7:
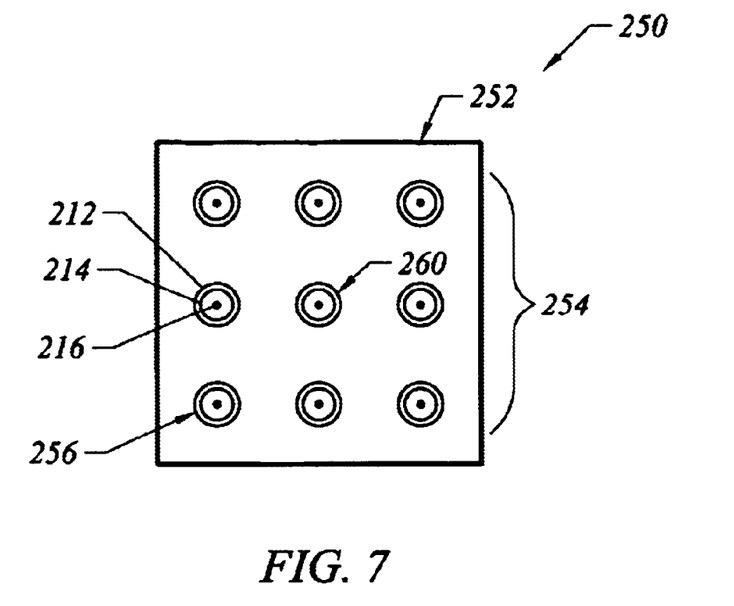
FIG. 7 is an end view of a third electrode assembly according to the present invention.
Figure 8:
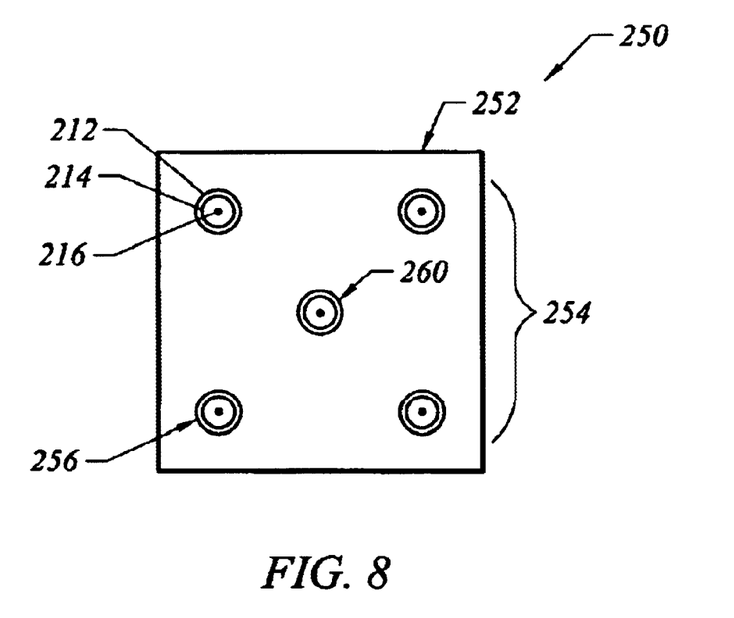
FIG. 8 is an end view of a fourth electrode assembly according to the present invention.

FIGS. 7 and 8 are distal end views of two more embodiments of the disposable tip shown in FIG. 6. In these embodiments, tip 250 comprises an electrode support 252 and an electrode assembly 254 comprising an array of electrodes 256 extending from support 252. In the embodiment shown in FIG. 7, the array includes nine electrodes 256, each having a guard 212, a proximal insulated portion 214 and a distal exposed portion 216 as in the previous embodiment. In FIG. 8, the array includes five electrodes 256, each having a guard 212, a proximal insulated portion 214 and a distal exposed portion 216. In both embodiments, the central electrode 260 will have an opposite polarity from the rest of the electrodes 256 to provide electric current flow therebetween. Thus, the electric current is generally confined to the region immediately surrounding the exposed portions 216 of the electrodes 256. Of course, other configurations are possible, such as providing the middle row or column of electrodes with the same polarity such that current flows between the two outer rows or columns and the middle row/or column. Alternatively, the device may be used in a monopolar modality with a dispersive return pad (not shown) that functions as the return electrode. Applicant has found, however, that the bipolar design helps to confine the electric current to the target region and thus, minimizes tissue damage that may occur with the monopolar design.

For particular applications, it may be desirable to further reduce the tissue temperature of the electrode/skin interface to further minimize damage to the epidermis layer. In one embodiment, the electrically conductive fluid, typically isotonic saline, is cooled prior to its delivery to the target site. Typically, the conductive fluid will be cooled to a temperature in the range of about 0°C. to 20° C., usually about 5° C. to 15° C. In addition, the probe may incorporate suction near the tip so that the conductive fluid is withdrawn from the target site after it has accomplished the function of providing a conductive path between the electrodes and the skin. These features accomplish two functions: (1) the conductive fluid that reaches the target site is cooler, which further reduces the tissue temperature; (2) as the electric fields increase the temperature of the conductive fluid around the electrodes, this hotter conductive fluid is aspirated from the target site; and (3) a convective cooling process is established by the cool fluid that moves through the target site and back through the aspiration lumen.

What is claimed is:

1. A method for treating wrinkles in a patient's skin comprising:

positioning first and second electrodes adjacent to, or in contact with, an outer surface of the patient's skin, where the electrodes are placed on either side of a wrinkle; and applying a sufficient high frequency voltage difference between the first and second electrodes such that electric current flows from the first electrode through target tissue in the patient's dermis layer to the second electrode without ablating the epidermis layer overlying the target tissue wherein the applying act comprises translating the electrodes alone the length of the wrinkle.

2. The method of claim 1 further comprising spacing the first and second electrodes a distance sufficient to cause the electric current to pass through the epidermis into the target tissue in the dermis layer.

3. The method of claim 1 further comprising spacing the first and second electrodes about 5 to 20 cm from each other.

4. The method of claim 1 further comprising minimizing current density in the epidermis during the applying step.

5. The method of claim 1 wherein the minimizing step is carried out by selecting electrode shapes that provide a homogenous current distribution around the electrodes.

6. The method of claim 1 wherein the first and second electrodes comprise rounded shapes with substantially no edges.

7. A method for treating wrinkles in a patient's skin comprising:

positioning first and second electrodes adjacent to, or in contact with, an outer surface of the patient's skin, where the electrodes are placed on either side of a wrinkle; and applying a sufficient high frequency voltage difference between the first and second electrodes such that electric current flows from the first electrode through target tissue in the patient's dermis layer to the second electrode without ablating the epidermis layer overlying the target tissue and wherein the method further comprising coating the electrode surfaces with an electrically conductive hydrogel and soaking the hydrogel with an electrically conductive liquid.

8. A system for treating wrinkles in a patient's skin comprising:
   an electrosurgical instrument having a shaft with a proximal end portion, a distal end portion and a first electrode on the distal end portion;
   a second electrode, where the first and second electrodes are adapted to be placed on a first side and a second side of a wrinkle;
   a power supply for applying a high frequency voltage difference between the first and second electrodes; and
   wherein the electrodes are configured such that, when the first and second electrodes are spaced from each other adjacent to, or in contact with, an outer surface of a patient's skin and a sufficient high frequency voltage difference is applied therebetween, electric current passes from the first electrode through target tissue in the patient's dermis to the second electrode without ablating the epidermis layer overlying the target tissue and wherein the first and second electrodes comprise electrically conductive hydrogel located at the surfaces of the first and second electrodes and wherein the hydro gel is soaked with an electrically conductive liquid.

9. The system of claim 8 wherein the second electrode is coupled to the electrosurgical instrument such that the first and second electrodes are spaced from each other by a distance of about 5 to 20 cm.

10. The system of claim 8 wherein the second electrode is coupled to the electrosurgical instrument such that the first and second electrodes are axially spaced a substantially equivalent distance from the instrument shaft.

11. The system of claim 8 wherein the first and second electrodes comprise rounded shapes with substantially no edges.

12. A system for treating wrinkles in a patient's skin comprising:
   an electrosurgical instrument having a shaft with a proximal end portion, a distal end portion and a first electrode on the distal end portion;
   a second electrode, where the first and second electrodes are adapted to be placed on a first side and a second side of a wrinkle;
   a power supply for applying a high frequency voltage difference between the first and second electrodes; and
   wherein the electrodes are configured such that, when the first and second electrodes are spaced from each other adjacent to, or in contact with, an outer surface of a patient's skin and a sufficient high frequency voltage difference is applied therebetween, electric current passes from the first electrode through target tissue in the patient's dermis to the second electrode without ablating the epidermis layer overlying the target tissue wherein the first and second electrodes comprise a spherical or hemispherical shape.

13. A method for treating wrinkles in a patient's skin comprising:
   positioning a first electrode and a second electrodes adjacent to, or in contact with, an outer surface of the patient's skin;
   coating a surface of the first and second electrodes with an electrically conductive hydrogel and soaking the hydrogel with an electrically conductive liquid; and
   applying a sufficient high frequency voltage difference between the first and second electrodes such that electric current flows from the first electrode through target tissue in the patient's dermis layer to the second electrode without ablating the epidermis layer overlying the target tissue.

14. A system for treating wrinkles in a patient's skin comprising:
   an electrosurgical instrument having a shaft with a proximal end portion, a distal end portion and a first electrode on the distal end portion;
   a second electrode, wherein the first and second electrodes comprise a spherical or hemispherical shape;
   a power supply for applying a high frequency voltage difference between the first and second electrodes; and
   wherein the electrodes are configured such that, when the first and second electrodes are spaced from each other adjacent to, or in contact with, an outer surface of a patient's skin and a sufficient high frequency voltage difference is applied therebetween, electric current passes from the first electrode through target tissue in the patient's dermis to the second electrode without ablating the epidermis layer overlying the target tissue.

15. A system for treating wrinkles in a patient's skin comprising:
   an electrosurgical instrument having a shaft with a proximal end portion, a distal end portion and a first electrode on the distal end portion;
   a second electrode, where the first and second electrodes are adapted to be placed on opposite sides of a wrinkle;
   an electrically conductive hydrogel coated on the surfaces of the first and second electrodes, wherein the hydrogel is soaked with an electrically conductive liquid;
   a power supply for applying a high frequency voltage difference between the first and second electrodes; and
   wherein the electrodes are configured such that, when the first and second electrodes are spaced from each other adjacent to, or in contact with, an outer surface of a patient's skin and a sufficient high frequency voltage difference is applied therebetween, electric current passes from the first electrode through target tissue in the patient's dermis to the second electrode without ablating the epidermis layer overlying the target tissue.

* * * * *